(12) United States Patent
Beard (10) Patent No.: US 11,150,888 B2
(45) Date of Patent: Oct. 19, 2021

(54) SOFTWARE BILL OF MATERIALS VALIDATION SYSTEMS AND METHODS

(71) Applicant: Daniel Ivan Beard, Tustin, CA (US)

(72) Inventor: Daniel Ivan Beard, Tustin, CA (US)

( * ) Notice: Subject to any disclaimer, the term of this patent is extended or adjusted under 35 U.S.C. 154(b) by 121 days.

(21) Appl. No.: 16/725,740

(22) Filed: Dec. 23, 2019

(65) Prior Publication Data

US 2020/0201620 A1 Jun. 25, 2020

Related U.S. Application Data

(60) Provisional application No. 62/784,416, filed on Dec. 22, 2018.

(51) Int. Cl.
| | | |
|---|---|---|
| *G06F 9/44* | (2018.01) | |
| *G06F 8/65* | (2018.01) | |
| *G16H 40/67* | (2018.01) | |
| *G06F 8/61* | (2018.01) | |
| *G06F 8/20* | (2018.01) | |

(52) U.S. Cl.
CPC .................. *G06F 8/65* (2013.01); *G06F 8/22* (2013.01); *G06F 8/61* (2013.01); *G16H 40/67* (2018.01)

(58) Field of Classification Search
None
See application file for complete search history.

(56) References Cited

U.S. PATENT DOCUMENTS

| | | | |
|---|---|---|---|
| 9,535,687 B2 | 1/2017 | Clemm et al. | |
| 9,712,385 B2 | 7/2017 | Taylor et al. | |
| 9,875,510 B1 | 1/2018 | Kasper | |
| 10,063,572 B2 | 8/2018 | Milazzo et al. | |
| 10,320,569 B1 | 6/2019 | Wentz et al. | |
| 2018/0088928 A1* | 3/2018 | Smith | G06F 8/65 |
| 2018/0211213 A1 | 7/2018 | Vivier et al. | |
| 2018/0219676 A1 | 8/2018 | Mattingly et al. | |
| 2018/0285217 A1 | 10/2018 | Smith et al. | |
| 2019/0141054 A1* | 5/2019 | Signorini | G06F 8/65 |
| 2019/0179806 A1* | 6/2019 | Reinsberg | H04L 9/3255 |
| 2019/0303541 A1 | 10/2019 | Reddy et al. | |
| 2019/0303579 A1 | 10/2019 | Reddy et al. | |
| 2019/0305957 A1 | 10/2019 | Reddy et al. | |
| 2019/0305959 A1 | 10/2019 | Reddy et al. | |
| 2019/0306173 A1 | 10/2019 | Reddy et al. | |
| 2019/0349426 A1 | 11/2019 | Smith et al. | |
| 2019/0354607 A1* | 11/2019 | Snow | H04L 67/22 |
| 2020/0084217 A1* | 3/2020 | Judka | H04L 63/101 |
| 2020/0287715 A1* | 9/2020 | Wang | H04L 9/0872 |

\* cited by examiner

*Primary Examiner* — Qamrun Nahar
(74) *Attorney, Agent, or Firm* — Total Awareness Consulting Services; Robert Winslow (57) ABSTRACT

Each of a plurality of medical devices is configured to generate a device specific Software Bill of Materials (SBOM), and communicate the device specific SBOM to a validator system(s). A central authority system(s) is configured to authorize the validator system(s) to add a new block(s) to a SBOM blockchain. The SBOM blockchain is structured to contain updates to the device specific SBOM. The validator system(s) is configured to create a local copy of the SBOM blockchain, build a SBOM hash tree based on data in the SBOM blockchain, search the SBOM hash tree for the device specific SBOM, add a new block to the SBOM blockchain, the new block comprising an update(s) to the device specific SBOM, validate the update(s) in the device specific SBOM based on a vulnerability database, and communicate the new block to at least one other validator system.

20 Claims, 8 Drawing Sheets

SOFTWARE BILL OF MATERIALS VALIDATION SYSTEMS AND METHODS

CROSS-REFERENCE TO RELATED APPLICATIONS

This application claims the benefit of U.S. Provisional Application No.: 62/784,416, filed Dec. 22, 2018, which is hereby incorporated by reference in its entirety.

BACKGROUND

In order to preserve the health of patients relying on medical devices, it is imperative to keep the medical devices secure from cyber threats. The manufactures of many existing medical devices may not be notified when additional software and/or hardware is installed on the medical devices after delivery to customers. The manufactures and/or administrators of many existing medical devices may not be notified when existing software and/or hardware is updated and/or removed from the medical devices after the medical devices are in operation. Administrators and/or users of many existing medical devices may not be aware that installed software and/or hardware may be vulnerable to cyber threats.

Many existing cybersecurity systems and methods developed for general purpose computing systems may not be applicable to medical devices. A variety of medical devices may involve a much larger variation in software and/or hardware configurations as compared to a variety of general purpose computing systems. Many existing cybersecurity systems and methods may prevent installation of additional software and/or hardware on medical devices. Many existing cybersecurity systems and methods may prevent installation of updates to existing software and/or hardware on medical devices. However, the installation of new software and/or hardware, and/or the installation of updates to existing software and/or hardware may be necessary for patient health, cybersecurity, medical device operations, communication with other medical devices, regulatory requirements, combinations thereof, and/or the like. The new software and/or hardware, and/or the updates to existing software and/or hardware, may be provided by entities other than the manufacturer of a medical device and/or the manufacturer of the operating system of a medical device.

Many manufactures of existing medical devices may establish acceptable health configurations for software and/or hardware on their medical devices. In addition, many existing medical devices are routinely tested for installed components. However, many manufactures may not be able to identify cyber threats, vulnerable software, and/or vulnerable hardware in every environment. Furthermore, standard configurations provided by the manufactures of existing medical devices may not meet administrator requirements for patient health, cybersecurity, medical device operations, communication with other medical devices, combinations thereof, and/or the like.

What is needed are improved systems and methods for validating software and/or hardware updates on medical devices.

DETAILED DESCRIPTION OF EMBODIMENTS

Embodiments of the present disclosure generate device specific Software Bill of Materials (SBOM) for medical devices. In this disclosure, medical devices may include medical appliances.

Embodiments of the present disclosure generate a SBOM blockchain. The SBOM blockchain may be employed to validate updates to a device specific SBOM for each of a plurality of medical devices. In this disclosure, updates to a device specific SBOM may include: installation of additional software, installation of additional hardware, removal of installed software, removal of installed hardware, combinations thereof, and/or the like.

Various embodiments may be employed to efficiently validate software and/or hardware installed on a medical device. The software and/or hardware may be validated to provide security to the medical device. Invalid software and/or hardware on an operational medical device may negatively impact the reliability of the medical device which may result in harm to one or more patients relying on the medical device. Software libraries installed on an operational medical device that are not employed for the primary function of the medical device may be vulnerable to cyber threats. Services running on an operational medical device that are not employed for the primary function of the medical device may be vulnerable to cyber threats.

Various embodiments may be employed to gain consensus on healthy installed software, healthy installed hardware, combinations thereof, and/or the like for one or more medical devices.

According to an embodiment, a device specific SBOM may be the same as an original SBOM for a specific medical device type when a specific medical device of the specific medical device type is first powered up in an operational environment. The medical device type may be based on a device configured to perform at least one medical function. The medical device type may be based on at least one medical condition. Over time, the device specific SBOM may be updated each time the software and/or hardware is updated on the specific medical device in operation.

According to an embodiment, a system may comprise a plurality of medical devices. The plurality of medical devices may be coupled to a computer network. Each of the plurality of medical devices may comprise a device processor. The device processor may comprise a plurality of processors. The plurality of processors may be distributed over a plurality of devices. Each of the plurality of medical devices may comprise a non-transitory machine readable device medium comprising device instructions. A device module may comprise the device instructions. The device instructions may be configured to cause the device processor to generate a device specific SBOM. The device specific SBOM may comprise a list of installed software and/or installed hardware. The installed software may comprise: software version(s), at least one library, library version(s), device operating system(s), operating system component(s), operating system version(s), patch(es) applied, patch version(s), combinations thereof, and/or the like. The installed hardware may comprise: device firmware, firmware version(s), combinations thereof, and/or the like. The device specific SBOM may comprise installed items provided by a plurality of entities or vendors. The device specific SBOM may be based on one of a plurality of enumerators. Each of the plurality of enumerators may be based on a hardware type, a hardware version, an operating system type, an operating system version, combinations thereof, and/or the like.

According to an embodiment, device instructions may be configured to generate a device specific SBOM through employment of meta information stored in at least one compiled library file. The device instructions may be configured to generate a device specific SBOM through employment of at least one hash of at least one compiled library. The at least one hash may be compared to at least one known hash of at least one library version. The device instructions may be configured to generate a device specific SBOM through employment of an operating system query. The device instructions may be configured to generate a device specific SBOM through employment of a package manager query.

According to an embodiment, device instructions may be configured to cause a device processor to communicate a device specific SBOM to at least one of a plurality of validator systems. The device specific SBOM may be communicated to a specific destination such as at least one central authority system and/or at least one validator system. A validator system and a medical device may share at least one hardware component. The device instructions may be configured to cause the device processor to generate the device specific SBOM on a regular basis. The device instructions may be configured to cause the device processor to generate the device specific SBOM according to a schedule. The device instructions may be configured to cause the device processor to generate the device specific SBOM during an idle mode. The idle mode may be based on the device processor, a non-transitory machine readable device medium, operations of a medical device, combinations thereof, and/or the like. The device instructions may be configured to cause the device processor to communicate the device specific SBOM upon boot up. The device instructions may be configured to cause the device processor to communicate the device specific SBOM in response to a determination that the device specific SBOM is distinct from a previous device specific SBOM.

According to an embodiment, device instructions may be configured to cause a device processor to generate at least one assertion. The at least one assertion may comprise a digital signature. The device instructions may be configured to cause the device processor to communicate the at least one assertion to at least one of a plurality of validator systems.

According to an embodiment, a system may comprise at least one central authority system. The at least one central authority system may be coupled to a computer network. Each of the at least one central authority system may comprise a central authority processor. The central authority processor may comprise a plurality of processors. The plurality of processors may be distributed over a plurality of systems. The at least one central authority system may comprise a non-transitory machine readable central authority medium comprising central authority instructions. The central authority instructions may be configured to cause the central authority processor to authorize a plurality of validator systems to add a new block to a SBOM blockchain. The SBOM blockchain may be structured to contain at least one update in a device specific SBOM for each of a plurality of medical devices.

According to an embodiment, a system may comprise a plurality of validator systems. The plurality of validator systems may be coupled to a computer network. The computer network may be in communication with a vulnerability database. Each of the plurality of validator systems may comprise a validator processor. The validator processor may comprise a plurality of processors. The plurality of processors may be distributed over a plurality of systems. Each of the plurality of validator systems may comprise a non-transitory machine readable validator medium comprising validator instructions. The validator instructions may be configured to cause the validator processor to create a local copy of a SBOM blockchain. The local copy may be based on blocks communicated from other validator systems. The validator instructions may be configured to cause the validator processor to build a SBOM hash tree. The SBOM hash tree may be based on data in the SBOM blockchain. The SBOM hash tree may comprise a root node with an original SBOM. The original SBOM may be based on a specific medical device type. The original SBOM may be provided with the medical device by a medical device manufacturer. The original SBOM may be the first SBOM generated once a specific medical device is put into operation. The root node may comprise SBOM data that is empty (NUL). The SBOM hash tree may comprise at least one leaf node. Each of the at least one leaf node may comprise a distinct SBOM update. The distinct SBOM update may comprise at least one update in a device specific SBOM. The distinct SBOM update may comprise at least one update from the original SBOM in the root node plus all of the previous distinct SBOM updates of the parent leaf nodes. In the case where the leaf node is directly connected to the root node, the distinct SBOM update may comprise at least one update from the original SBOM in the root node. Therefore, a device specific SBOM may be equivalent to a combination of the original SBOM and all of the distinct SBOM updates in all of the parent leaf nodes. In the case where the SBOM data in the root node is empty, each of the leaf nodes directly connected to the root node may comprise a distinct SBOM update that is equivalent to a device specific SBOM communicated from a medical device.

According to an embodiment, validator instructions may be configured to cause a validator processor to search a SBOM hash tree for a device specific SBOM. The search may comprise attempting to reconstruct a copy of the device specific SBOM through traversal of the root node and at least one leaf node. The validator instructions may be configured to cause the validator processor to add a new block to a SBOM blockchain in response to the device specific SBOM not being completely contained in the SBOM hash tree. The new block may comprise at least one update in the device specific SBOM from a previous device specific SBOM. The new block may comprise device specific SBOM changes from at least one medical device. The validator instructions may be configured to cause the validator processor to validate at least one update in the device specific SBOM based on a vulnerability database. The new block may comprise device specific SBOM changes communicated from at least one medical device. The validator instructions may be configured to cause the validator processor to validate at least one update in the device specific SBOM in response to the device specific SBOM not being completely contained in the SBOM hash tree. A request for validation may be communicated to a central authority system. New entries may be added to the vulnerability database in response to at least one of the at least one update in the device specific SBOM not being contained in the vulnerability database. The validator instructions may be configured to cause the validator processor to communicate the new block to at least one other validator system in the plurality of validator systems in response to the new block being added to the SBOM blockchain. The validator instructions may be configured to cause the validator processor to generate a SBOM score. The SBOM score may be based on the device specific SBOM and the vulnerability database. The validator instructions may be configured to cause the validator processor to add the SBOM score to the new block.

According to an embodiment, a device specific SBOM may be based on an installed application, an installed library, an installed operating system, a hardware configuration, combinations thereof, and/or the like.

According to an embodiment, a system may comprise a coordinator system. The coordinator system may comprise a coordinator processor. The coordinator processor may comprise a plurality of processors. The plurality of processors may be distributed over a plurality of systems. The coordinator system may comprise a non-transitory machine readable coordinator medium comprising coordinator instructions. The coordinator instructions may be configured to cause the coordinator processor to generate status data. The status data may comprise alerts, an inventory of medical devices, an inventory of validator systems, a list of distinct SBOM updates, a list of validated distinct SBOM updates, at least one device specific SBOM, combinations thereof, and/or the like. The status data may be communicated to at least one client system.

Figure 1:
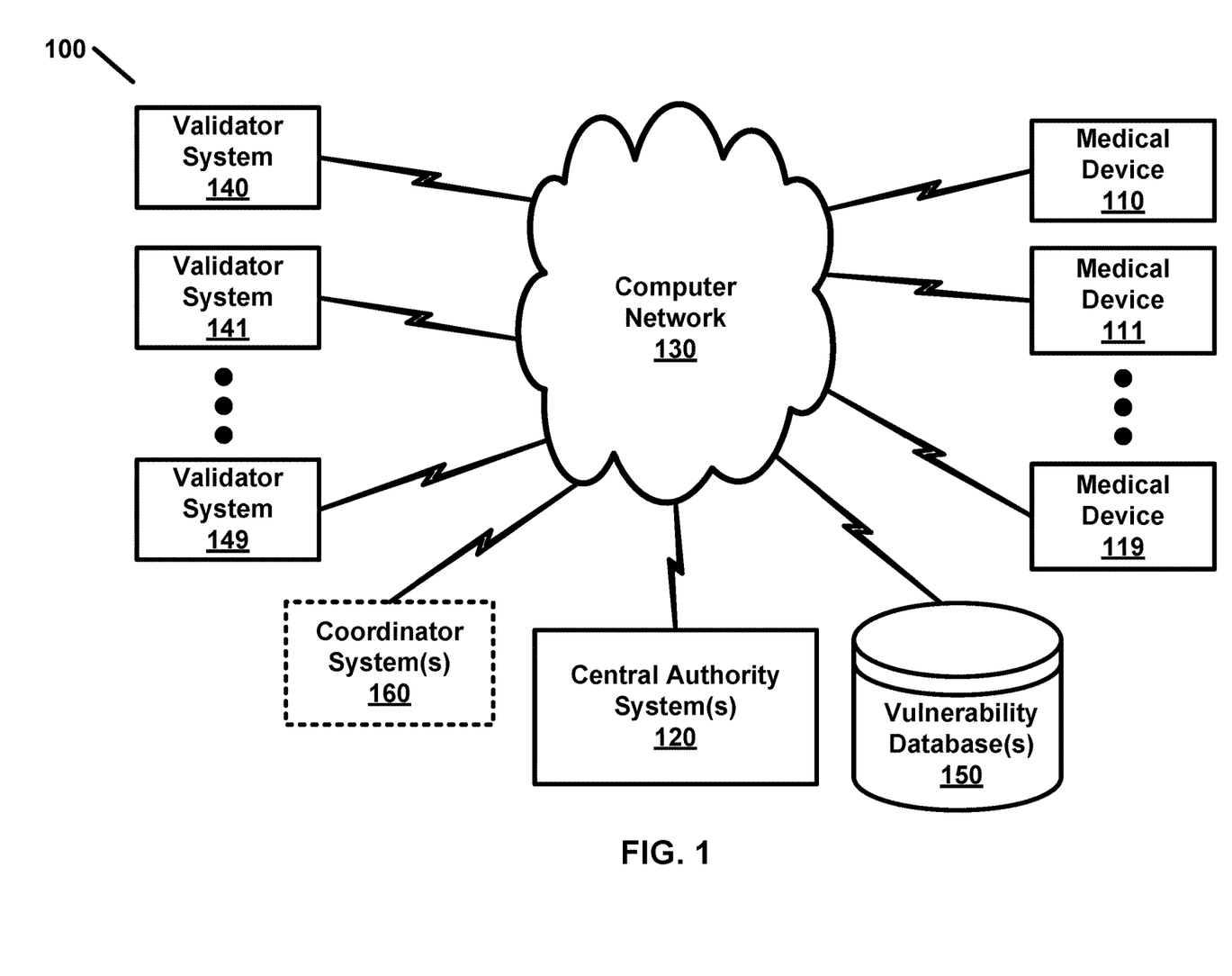
FIG. 1 is an example block diagram showing a Software Bill of Materials (SBOM) validation system as per an aspect of the disclosure.

FIG. 1 is an example block diagram showing a SBOM validation system 100 as per an aspect of the disclosure. The SBOM validation system 100 may comprise a plurality of medical devices (110, 111 . . . 119). The plurality of medical devices (110, 111 . . . 119) may be in communication with computer network 130. The SBOM validation system 100 may comprise at least one central authority system 120. The at least one central authority system 120 may be in communication with the computer network 130. The SBOM validation system 100 may comprise s plurality of validator systems (140, 141 . . . 149). The plurality of validator systems (140, 141 . . . 149) may be in communication with the computer network 130. The computer network 130 may be in communication with at least one vulnerability database 150. At least one of the at least one vulnerability database 150 may be remote from the SBOM validation system 100. At least one of the at least one vulnerability database 150 may be part of the SBOM validation system 100. The SBOM validation system 100 may comprise at least one coordinator system 160. The at least one coordinator system 160 may be in communication with the computer network 130.

Figure 2:
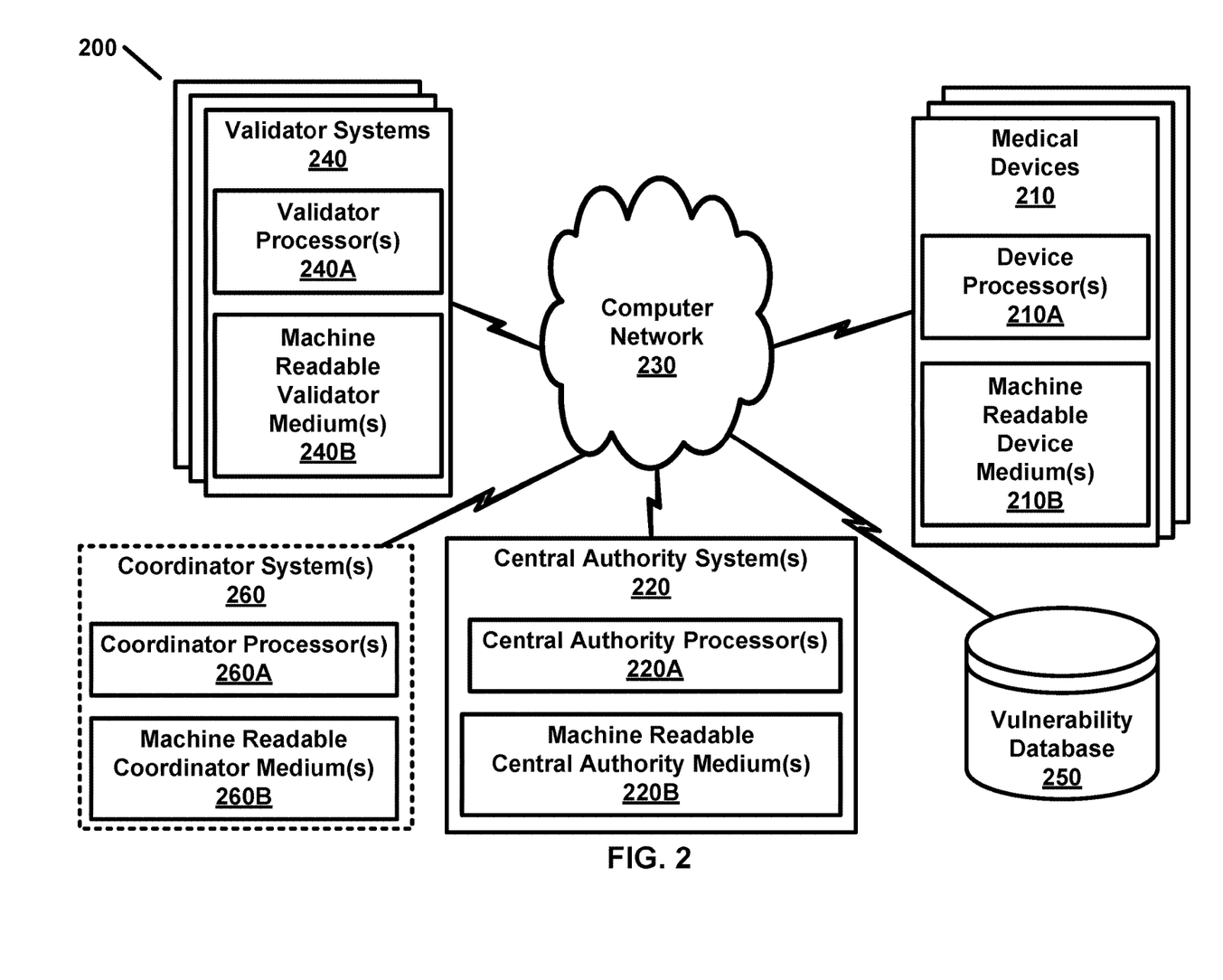
FIG. 2 is an example block diagram showing a SBOM validation system as per an aspect of the disclosure.

FIG. 2 is an example block diagram showing a SBOM validation system 200 as per an aspect of the disclosure. The SBOM validation system 200 may comprise a plurality of medical devices 210. Each of the plurality of medical devices 210 may be in communication with computer network 230. Each of the plurality of medical devices 210 may comprise at least one device processor 210A. Each of the plurality of medical devices 210 may comprise at least one machine readable device medium 210B. The SBOM validation system 200 may comprise at least one central authority system 220. Each of the at least one central authority system 220 may be in communication with the computer network 230. Each of the at least one central authority system 220 may comprise at least one central authority processor 220A. Each of the at least one central authority system 220 may comprise at least one machine readable central authority medium 220B. The SBOM validation system 200 may comprise a plurality of validator systems 240. Each of the plurality of validator systems 240 may be in communication with the computer network 230. Each of the plurality of validator systems 240 may comprise at least one validator processor 240A. Each of the plurality of validator systems 240 may comprise at least one machine readable validator medium 240B. The computer network 230 may be in communication with a vulnerability database 250. The SBOM validation system 200 may comprise at least one coordinator system 260. Each of the at least one coordinator system 260 may be in communication with the computer network 230. Each of the at least one coordinator system 260 may comprise at least one coordinator processor 260A. Each of the at least one coordinator system 260 may comprise at least one machine readable coordinator medium 260B.

Figure 3:
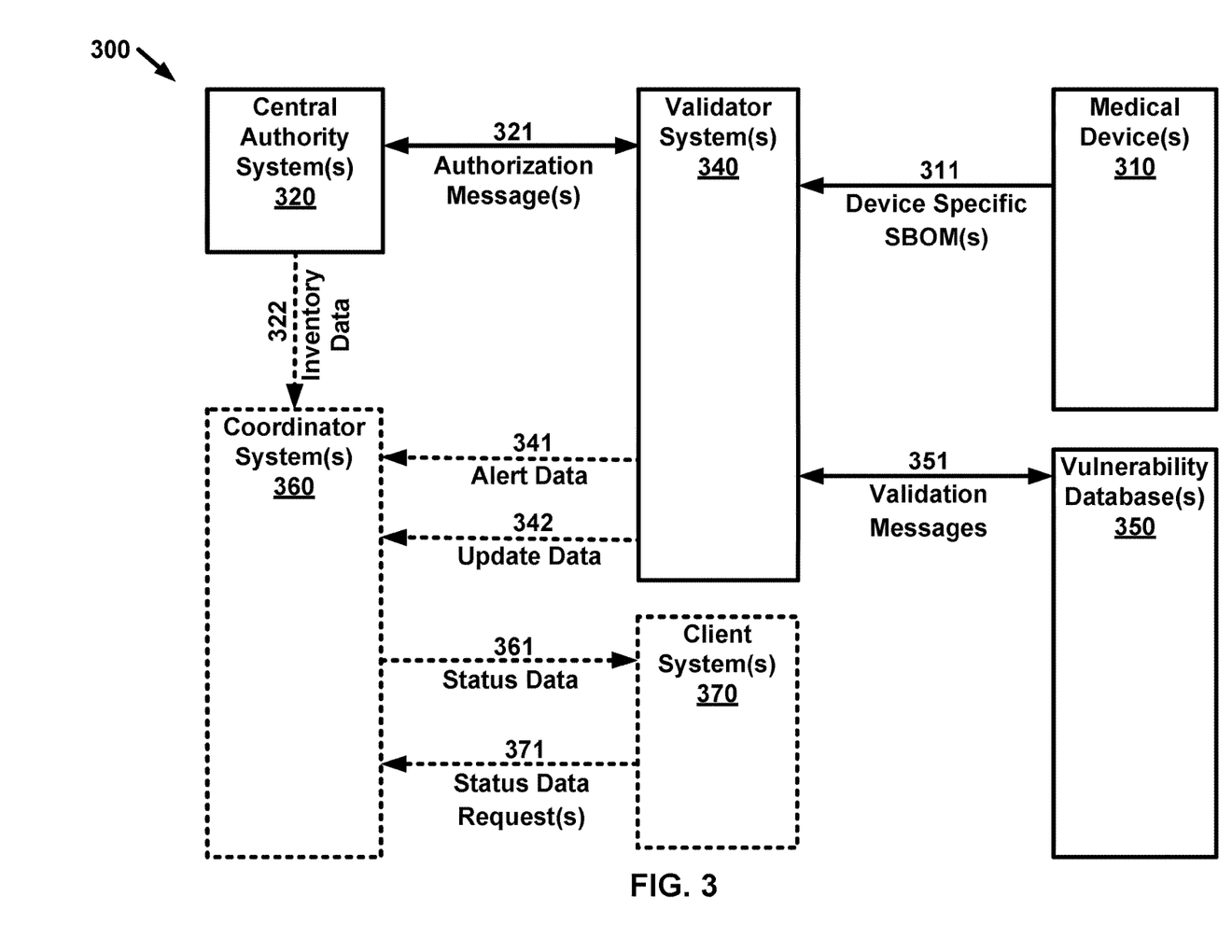
FIG. 3 is an example block diagram showing a SBOM validation system as per an aspect of the disclosure.

FIG. 3 is an example block diagram showing a SBOM validation system 300 as per an aspect of the disclosure. The SBOM validation system 300 may comprise a plurality of medical devices 310. The SBOM validation system 300 may comprise at least one central authority system 320. The SBOM validation system 300 may comprise a plurality of validator systems 340. The SBOM validation system 300 may be in communication with at least one vulnerability database 350. The SBOM validation system 300 may comprise at least one coordinator system 360. The at least one coordinator system 360 may be in communication with at least one client system 370. Each of the plurality of medical devices 310 may be configured to communicate a device specific SBOM 311 to at least one of the plurality of validator systems 340. Each of the plurality of validator systems 340 may be configured to communicate authorization messages 321 to the at least one central authority system 320. Each of the plurality of validator systems 340 may be configured to communicate alert data 341 to the at least one coordinator system 360. Each of the plurality of validator systems 340 may be configured to communicate update data 342 to the at least one coordinator system 360. Each of the plurality of validator systems 340 may be configured to communicate validation messages 351 to the at least one vulnerability database 350. The at least one central authority system 320 may be configured to communicate authorization messages 321 to the plurality of validator systems 340. The at least one central authority system 320 may be configured to communicate inventory data 322 to the at least one coordinator system 360. The at least one coordinator system 360 may be configured to communicate status data 361 to at least one client system 370. At least one of the at least one client system 370 may be configured to communicate status data requests 371 to at least one of the at least one coordinator system 360. The at least one vulnerability database 350 may be configured to communicate validation messages 351 to at least one of the plurality of validator systems 340.

Figure 4:
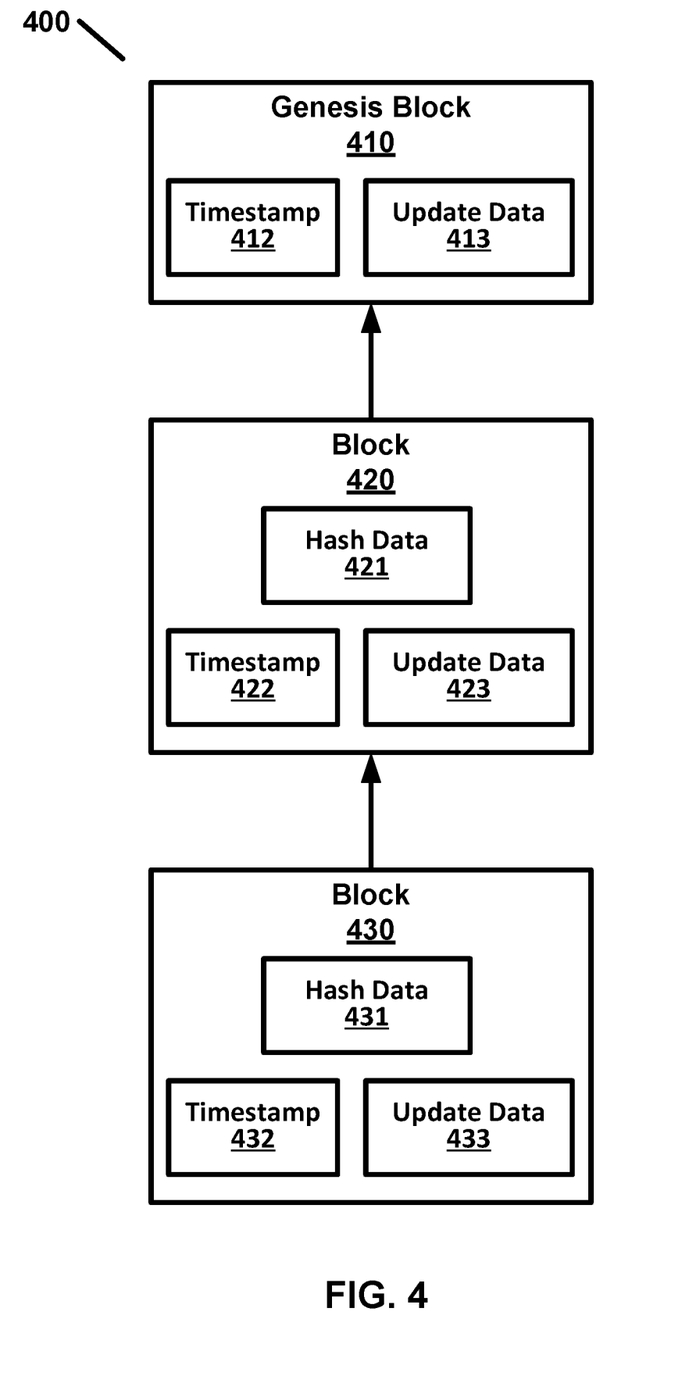
FIG. 4 is an example block diagram showing a SBOM blockchain as per an aspect of the disclosure.

FIG. 4 is an example block diagram showing a SBOM blockchain 400 as per an aspect of the disclosure. The SBOM blockchain 400 may comprise a genesis block 410. The genesis block 410 may comprise a timestamp 412. The genesis block 410 may comprise update data 413. Update data 413 may comprise an original SBOM. Update data 413 may be empty (NUL). The SBOM blockchain 400 may comprise block 420. Block 420 may comprise hash data 421 linking block 420 to the genesis block 410. Block 420 may comprise a timestamp 422. Block 420 may comprise update data 423. The SBOM blockchain 400 may comprise block 430. Block 430 may comprise hash data 431 linking block 430 to block 420. Block 430 may comprise a timestamp 432. Block 430 may comprise update data 433. Update data (413, 423, and 433) may comprise distinct SBOM updates for at least some of a plurality of medical devices. In the case where update date 413 is empty, update data 423 may comprise at least one distinct SBOM update that is equivalent to at least one device specific SBOM that is communicated from at least one medical device. Update data (413, 423, and 433) may comprise identification information for at least some of the plurality of medical devices. The plurality of medical devices may comprise a plurality of medical device types. The plurality of medical devices may comprise at least one specific medical device type. The plurality of medical devices may comprise medical devices manufactured by at least one medical device manufacturer. The plurality of medical devices may comprise medical devices manufactured by a single medical device manufacturer.

Figure 5:
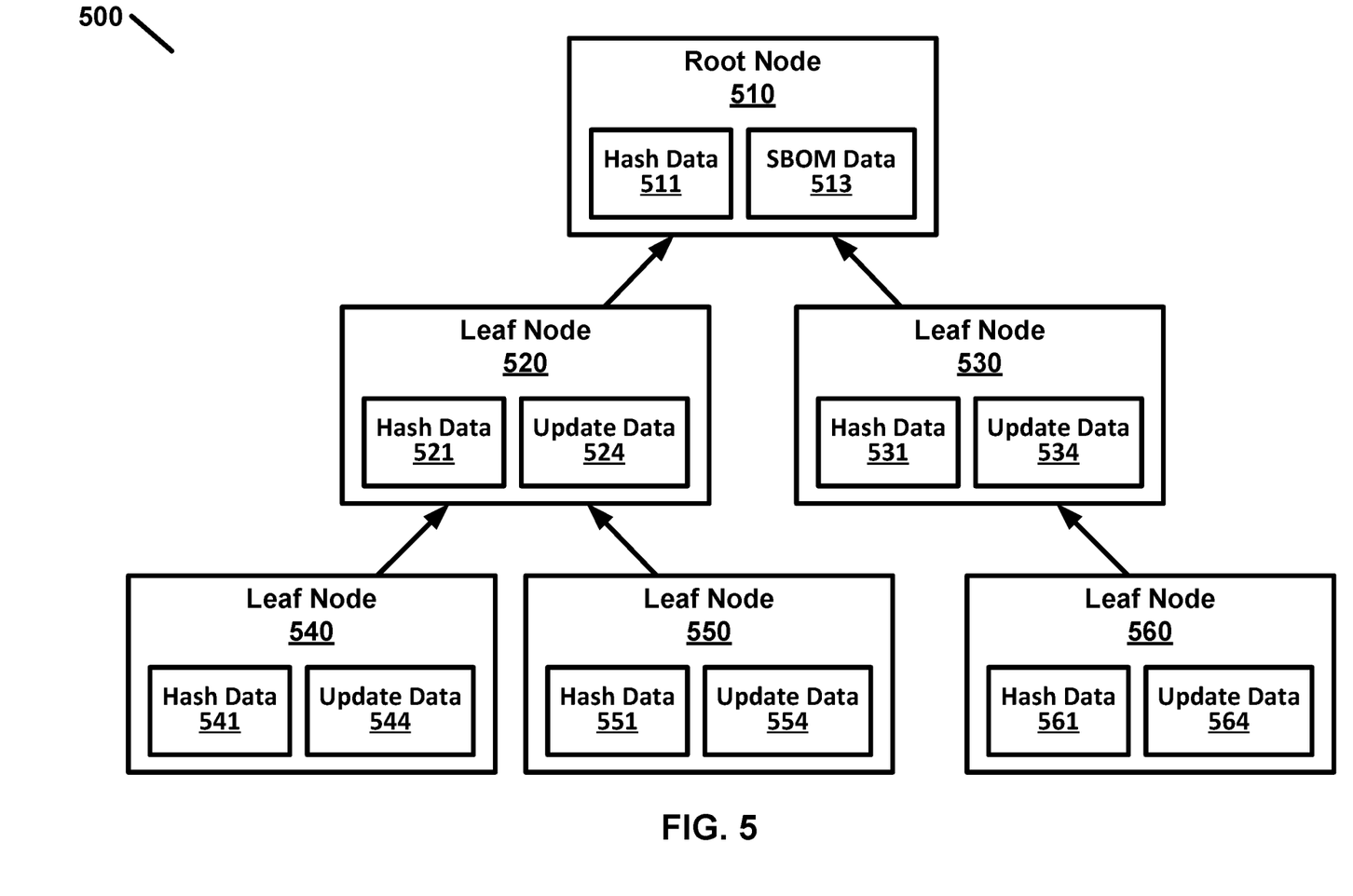
FIG. 5 is an example block diagram showing a SBOM hash tree as per an aspect of the disclosure.

FIG. 5 is an example block diagram showing a SBOM hash tree 500 as per an aspect of the disclosure. The SBOM hash tree 500 may comprise a root node 510. The SBOM hash tree 500 may comprise leaf nodes (520, 530, 540, 550, and 560). The root node 510 may comprise hash data 511. The hash data 511 may comprise a hash of SBOM data 513. The hash data 511 may be empty (NUL). The root node 510 may comprise SBOM data 513. The SBOM data 513 may comprise an original SBOM. The SBOM data 513 may be empty (NUL). Leaf node 520 may comprise hash data 521. Leaf node 520 may comprise update data 524. The hash data 521 may be based on the hash of: root node 510 and the update data 524. The update data 524 may comprise at least one update to the original SBOM in SBOM data 513. Leaf node 530 may comprise hash data 531. Leaf node 530 may comprise update data 534. The hash data 531 may be based on the hash of: root node 510 and the update data 534. The update data 534 may comprise at least one update to the original SBOM in SBOM data 513. Leaf node 540 may comprise hash data 541. Leaf node 540 may comprise update data 544. The hash data 541 may be based on the hash of: leaf node 520 and the update data 544. The update data 544 may comprise at least one update to: the original SBOM in SBOM data 513 plus the update(s) in update data 524. Leaf node 550 may comprise hash data 551. Leaf node 550 may comprise update data 554. The hash data 551 may be based on the hash of: leaf node 520 and the update data 554. The update data 554 may comprise at least one update to: the original SBOM in SBOM data 513 plus the update(s) in update data 524. Leaf node 560 may comprise hash data 561. The hash data 561 may be based on the hash of: leaf node 530 and the update data 564. The update data 564 may comprise at least one update to: the original SBOM in SBOM data 513 plus the update(s) in update data 534. Data in each of the update data (524, 534, 544, 554, and 564) may be distinct.

According to an embodiment, a device specific SBOM may be generated for each of a plurality of medical devices. The device specific SBOM may be communicated to at least one of a plurality of validator systems. A SBOM hash tree may be built based on data in a SBOM blockchain. The SBOM hash tree may comprise a root node with an original SBOM. The SBOM hash tree may comprise at least one leaf node. Each of the at least one leaf node may comprise a distinct SBOM update. The SBOM hash tree may be searched for a device specific SBOM. A new block may be added to the SBOM blockchain in response to the device specific SBOM not being contained in the SBOM hash tree. The new block may comprise a new distinct SBOM update. The new distinct SBOM update may be validated based on a vulnerability database. Validation may comprise a result such as, for example, "unknown" if a SBOM update does not exist in the vulnerability database. In this example, the SBOM update may be added to the vulnerability database. In this example, SBOM updates that do not exist in the vulnerability database may be ignored. The new block may be communicated to at least one of the plurality of validator systems in response to the new block being added to the SBOM blockchain.

According to an embodiment, consensus may be gained from a majority of a plurality of validator systems. The consensus may be based on a SBOM blockchain. The consensus may be based on one or more blocks of the SBOM blockchain. The consensus may be based on a vulnerability database.

According to an embodiment, a SBOM score may be generated. The SBOM score may be based on a device specific SBOM and/or a vulnerability database. The SBOM score may be added to a new block of a SBOM blockchain.

According to an embodiment, status data may be generated.

Figure 6:
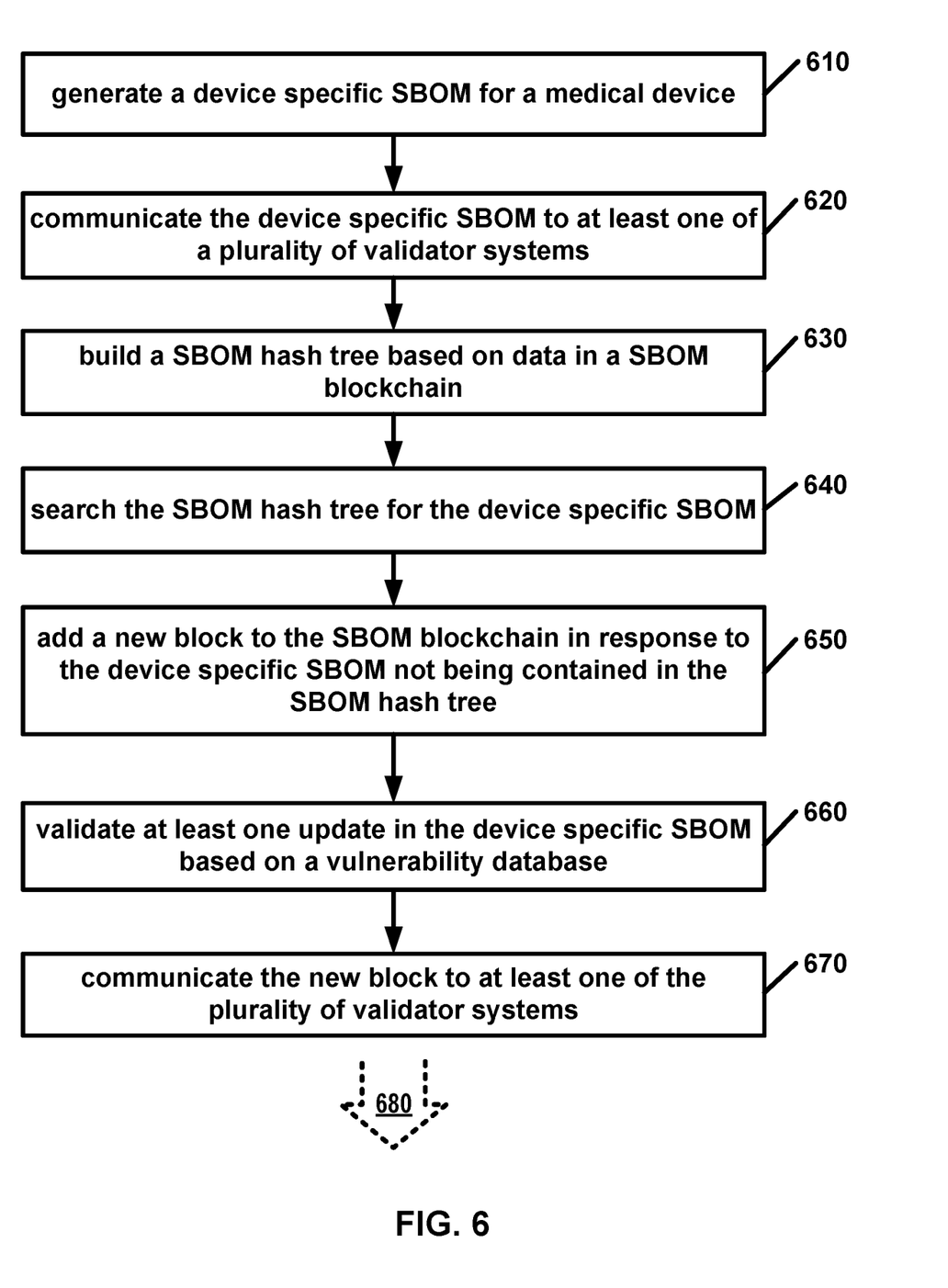
FIG. 6 is an example flow diagram of validating at least one update in a device specific SBOM as per an aspect of the disclosure.

FIG. 6 is an example flow diagram of validating at least one update in a device specific SBOM as per an aspect of the disclosure. A device specific SBOM may be generated for a medical device at 610. The device specific SBOM may be communicated to at least one of a plurality of validator systems at 620. A SBOM hash tree may be built based on data in a SBOM blockchain at 630. The SBOM hash tree may comprise a root node with an original SBOM. The SBOM hash tree may comprise at least one leaf node each comprising a distinct SBOM update. The SBOM hash tree may be searched for the device specific SBOM at 640. A new block may be added to the SBOM blockchain in response to the device specific SBOM not being contained in the SBOM hash tree at 650. The new block may comprise at least one update in the device specific SBOM from a previous device specific SBOM. The previous device specific SBOM may be based on the original SBOM. The previous device specific SBOM may be based on at least one SBOM update in at least one parent leaf node. At least one update in the device specific SBOM may be validated based on a vulnerability database at 660. The new block may be communicated to at least one of the plurality of validator systems in response to the new block being added to the SBOM blockchain at 670. Additional processing may take place at 680. The additional processing may include any combination of the processing examples in FIG. 7A, FIG. 7B, and FIG. 7C.

Figure 7A:
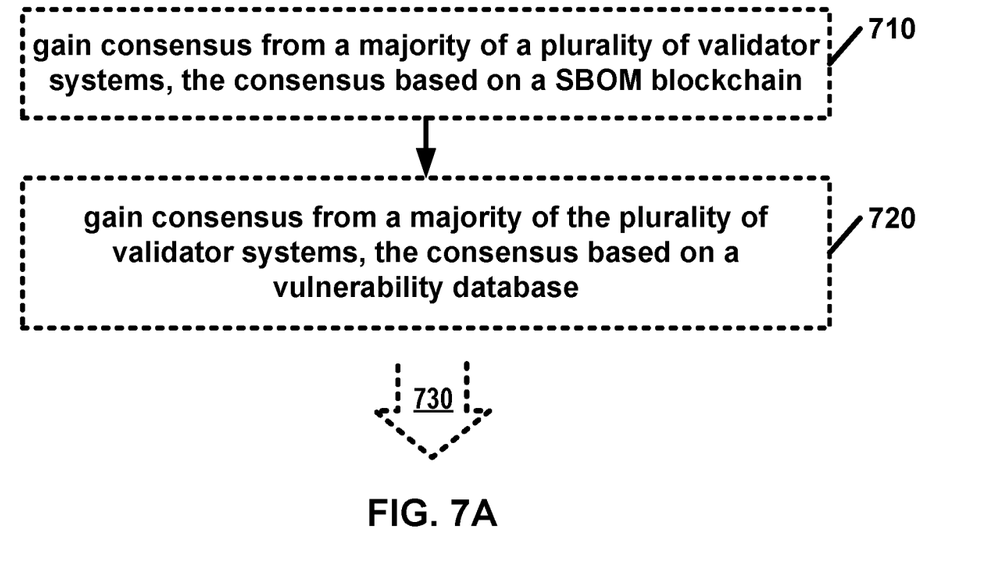
FIG. 7A is an example flow diagram of gaining consensus from a plurality of validator systems as per an aspect of the disclosure.

FIG. 7A is an example flow diagram of gaining consensus from a plurality of validator systems as per an aspect of the disclosure. Consensus may be gained from a majority of a plurality of validator systems at 710. The consensus may be based on a SBOM blockchain. Consensus may be gained from a majority of the plurality of validator systems at 720. The consensus may be based on a vulnerability database. The vulnerability database may comprise at least one vulnerability identification. The vulnerability database may comprise at least one vulnerability score. Additional processing may take place at 730. The additional processing may include any combination of the processing examples in FIG. 7B and FIG. 7C.

Figure 7B:
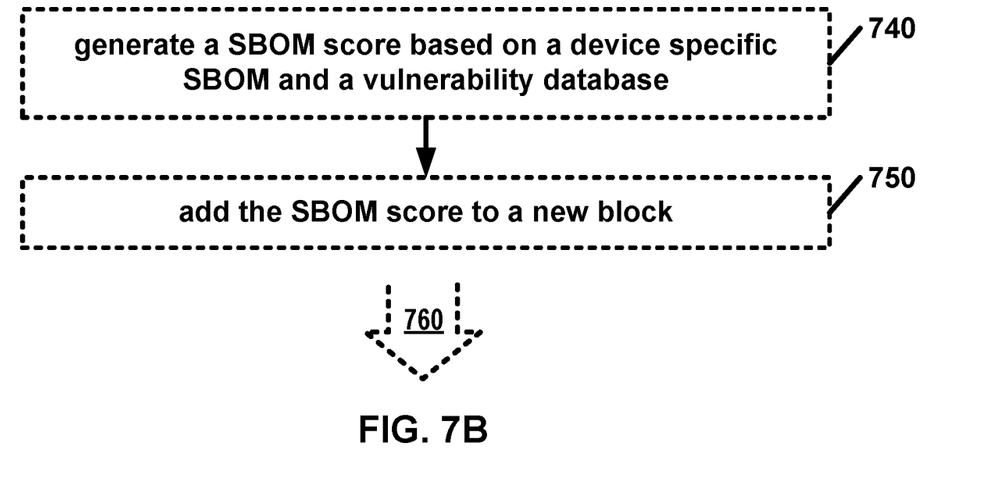
FIG. 7B is an example flow diagram of generating a SBOM score as per an aspect of the disclosure.

FIG. 7B is an example flow diagram of generating a SBOM score as per an aspect of the disclosure. A SBOM score may be generated at 740. The SBOM score may be based on a device specific SBOM. The SBOM score may be based on a vulnerability database. The SBOM score may be added to a new block at 750. Additional processing may take place at 760. The additional processing may include any combination of the processing examples in FIG. 7A and FIG. 7C.

Figure 7C:
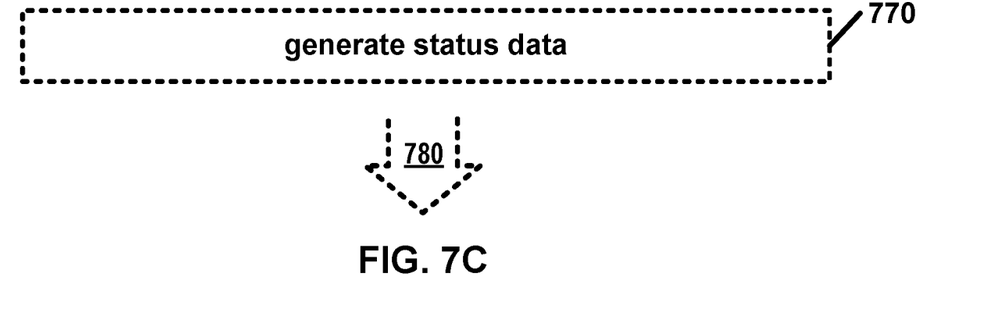
FIG. 7C is an example flow diagram of generating status data as per an aspect of the disclosure.

FIG. 7C is an example flow diagram of generating status data as per an aspect of the disclosure. Status data may be generated at 770. Additional processing may take place at 780. The additional processing may include any combination of the processing examples in FIG. 7A and FIG. 7B.

Figure 8:
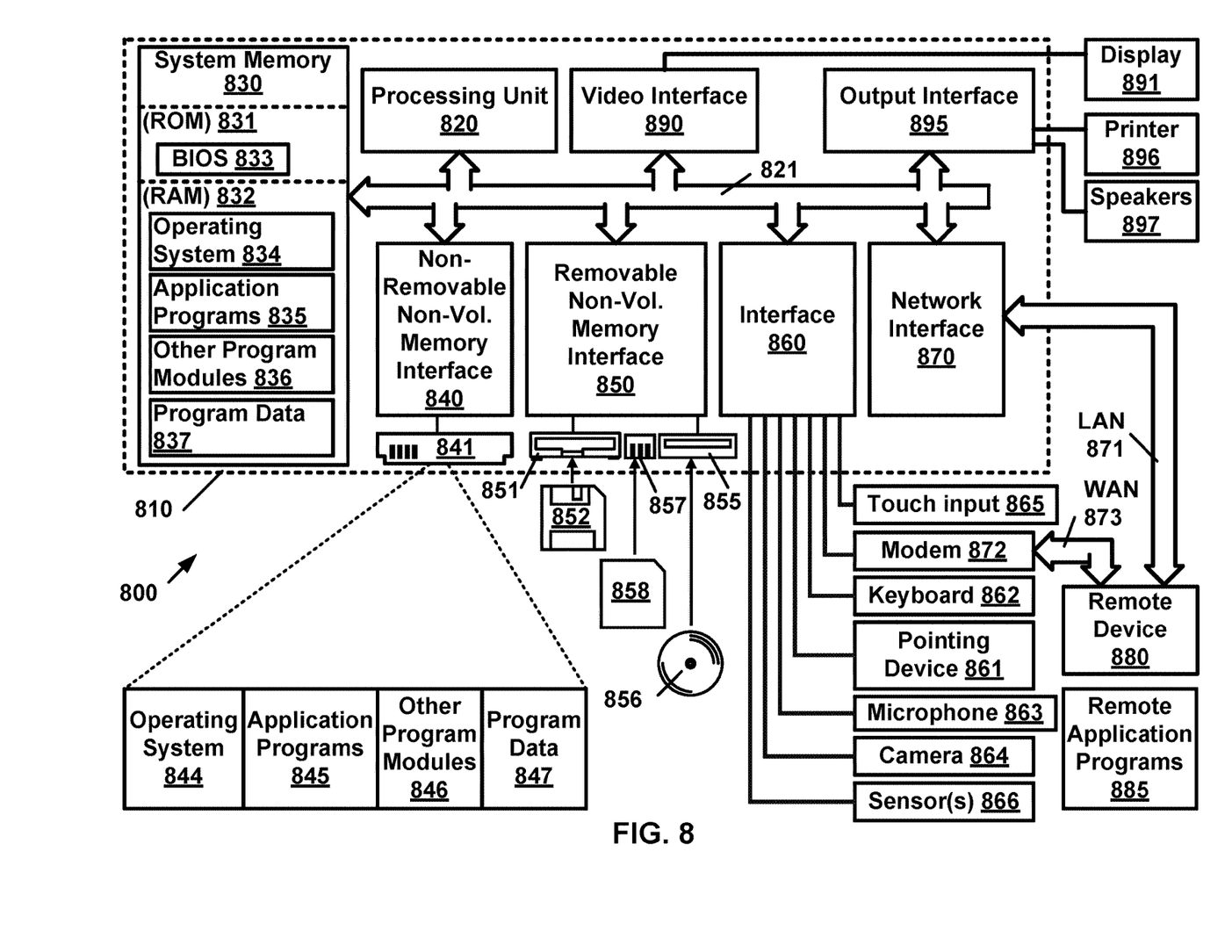
FIG. 8 is a block diagram of a medical device in which aspects of the disclosure may be practiced.

FIG. 8 is a block diagram of a medical device in which aspects of the disclosure may be practiced. The medical device may comprise computing device 810. Components of computing device 810 may include, but are not limited to, a processing unit 820, a system memory 830, and a system bus 821 that couples various system components including the system memory 830 to the processing unit 820.

Computing device 810 may comprise a variety of computer readable media. Computer readable media may be available media accessible by computing device 810 and may include both volatile and nonvolatile media, removable and non-removable media. By way of example, and not limitation, computer readable media may comprise computer storage media and communication media. Computer storage media may comprise both volatile and nonvolatile, removable and non-removable media implemented in a method or technology for storage of data such as computer readable instructions, data structures, program modules, other data, combinations thereof, and/or the like. Computer storage media may comprise, but is not limited to, random access memory (RAM), read-only memory (ROM), electrically erasable programmable read-only memory (EEPROM), flash memory or other memory technology, compact disc read-only memory (CD-ROM), digital versatile disks (DVD) or other optical disk storage, magnetic cassettes, magnetic tape, magnetic disk storage or other magnetic storage devices, and/or any other medium which may be employed to store data and which may be accessed by computing device 810. Communication media may comprise computer readable instructions, data structures, program modules and/or other data in a modulated data signal such as a carrier wave and/or other transport mechanism and may comprise data delivery media. The term "modulated data signal" means a signal that has one or more of its characteristics set or changed in such a manner as to encode data in the signal. By way of example, and not limitation, communication media includes wired media such as a wired network or direct-wired connection, and wireless media such as acoustic, radio frequency (RF), infrared and other wireless media. Combinations of any of the above may also be included within the scope of computer readable media.

The system memory 830 may comprise computer storage media in the form of volatile and/or nonvolatile memory such as ROM 831 and RAM 832. A basic input/output system 833 (BIOS), containing the basic routines that help to transfer data between elements within computing device 810, such as during start-up, may be stored in ROM 831. RAM 832 may comprise data and/or program modules that may be accessible to and/or presently being operated on by processing unit 820. By way of example, and not limitation, FIG. 8 illustrates operating system 834, application programs 835, other program modules 836, and program data 837.

The computing device 810 may also comprise other removable/non-removable volatile/nonvolatile computer storage media. By way of example only, FIG. 8 illustrates a hard disk drive 841 that may read from or write to non-removable, nonvolatile magnetic media, a magnetic disk drive 851 that may read from or write to a removable, nonvolatile magnetic disk 852, a flash drive reader 857 that may read flash drive 858, and an optical disk drive 855 that may read from or write to a removable, nonvolatile optical disk 856 such as a CD ROM or other optical media. Other removable/non-removable, volatile/nonvolatile computer storage media that may be used in the operating environment include, but are not limited to, magnetic tape cassettes, flash memory cards, digital versatile disks, digital video tape, solid state RAM, solid state ROM, and the like. The hard disk drive 841 may be connected to the system bus 821 through a non-removable memory interface such as interface 840, and magnetic disk drive 851 and optical disk drive 855 may be connected to the system bus 821 by a removable memory interface, such as interface 850.

The drives and their associated computer storage media discussed above and illustrated in FIG. 8 provide storage of computer readable instructions, data structures, program modules and other data for the computing device 810. In FIG. 8, for example, hard disk drive 841 is illustrated as storing operating system 844, application programs 845, program data 847, and other program modules 846. Additionally, for example, non-volatile memory may include instructions for presenting images on a display 891 of computing device 810 and/or the like. Similarly, non-volatile memory may comprise instructions for causing the presentation of images on the display of a remote device 880 and/or the like. Display 891 and touch input 865 may be integrated into the same device.

A user may enter commands and data into computing device 810 through input devices such as a touch input device 865, a keyboard 862, a microphone 863, a camera 864, and a pointing device 861, such as a mouse, trackball or touch pad. These and other input devices may be connected to the processing unit 820 through interface 860 coupled to system bus 821, but may be connected by other interface and bus structures, such as a parallel port, game port or a universal serial bus (USB). Data from at least one sensors 866 may be may be communicated to the processing unit 820 through interface 860 coupled to system bus 821. The at least one sensor 866 may be local and/or remote to the medical device 800. A display 891 or other type of display device may be connected to the system bus 821 via an interface, such as a video interface 890. Other devices, such as, for example, speakers 897 and printer 896 may be connected to the system via output interface 895.

The computing device 810 may be operated in a networked environment using logical connections to one or more remote devices, such as a remote device 880. Remote device 880 may be a hand-held device, a server, a router, a peer medical device, a validator system, or a central authority system, and typically includes many or all of the elements described above relative to the computing device 810.

The logical connections depicted in FIG. 8 include a local area network (LAN) 871 and a wide area network (WAN) 873, but may also include other networks. Such networking environments are commonplace in hospitals, treatment centers, intranets, and the Internet.

When used in a LAN networking environment, the computing device 810 is connected to the LAN 871 through a network interface or adapter 870. When used in a WAN networking environment, the computing device 810 may comprise a modem 872 or other means for establishing communications over the WAN 873, such as the Internet. The modem 872, which may be internal or external, may be connected to the system bus 881 via interface 860, or other appropriate mechanism. The modem 872 may be wired or wireless. Examples of wireless devices may comprise, but are not limited to: Wi-Fi and Bluetooth. In a networked environment, program modules depicted relative to the computing device 810, or portions thereof, may be stored in the remote memory storage device. By way of example, and not limitation, FIG. 8 illustrates remote application programs 885 as residing on remote device 880. It will be appreciated that the network connections shown are presented as examples only and other means of establishing a communications link between the devices may be used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

In this specification, "a" and "an" and similar phrases are to be interpreted as "at least one" and "one or more." References to "a", "an", and "one" are not to be interpreted as "only one". In this specification, the term "may" is to be interpreted as "may, for example." In other words, the term "may" is indicative that the phrase following the term "may" is an example of one of a multitude of suitable possibilities that may, or may not, be employed to one or more of the various embodiments. In this specification, the phrase "based on" is indicative that the phrase following the term "based on" is an example of one of a multitude of suitable possibilities that may, or may not, be employed to one or more of the various embodiments. References to "an" embodiment in this disclosure are not necessarily to the same embodiment.

Many of the elements described in the disclosed embodiments may be implemented as modules. A module is defined here as an isolatable element that performs a defined function and has a defined interface to other elements. The modules described in this disclosure may be implemented in hardware, a combination of hardware and software, firmware, wetware (i.e. hardware with a biological element) or a combination thereof, all of which are behaviorally equivalent. For example, modules may be implemented using computing hardware in combination with software routine(s) written in a computer language (Java, HTML, XML, PHP, Python, ActionScript, JavaScript, Ruby, Prolog, SQL, VBScript, Visual Basic, Perl, C, C++, Objective-C or the like). Additionally, it may be possible to implement modules using physical hardware that incorporates discrete or programmable analog, digital and/or quantum hardware. Examples of programmable hardware include: computers, microcontrollers, microprocessors, application-specific integrated circuits (ASICs), field programmable gate arrays (FPGAs), and complex programmable logic devices (CPLDs). Computers, microcontrollers and microprocessors are programmed using languages such as assembly, C, C++ or the like. FPGAs, ASICs and CPLDs are often programmed using hardware description languages (HDL) such as VHSIC hardware description language (VHDL) or Verilog that configure connections between internal hardware modules with lesser functionality on a programmable device. Finally, it needs to be emphasized that the above mentioned technologies may be used in combination to achieve the result of a functional module.

Some embodiments may employ processing hardware. Processing hardware may include one or more processors, computer equipment, embedded system, machines and/or the like. The processing hardware may be configured to execute instructions. The instructions may be stored on a machine-readable medium. According to some embodiments, the machine-readable medium (e.g. automated data medium) may be a medium configured to store data in a machine-readable format that may be accessed by an automated sensing device. Examples of machine-readable media include: magnetic disks, cards, tapes, and drums, flash memory, memory cards, electrically erasable programmable read-only memory (EEPROM), solid state drives, optical disks, barcodes, magnetic ink characters, and/or the like.

While various embodiments have been described above, it should be understood that they have been presented by way of example, and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments. Thus, the present embodiments should not be limited by any of the above described exemplary embodiments. In particular, it should be noted that, for example purposes, validation systems have been described as including a computing systems and medical devices. However, one skilled in the art will recognize that the computing system and medical device may vary from a traditional server/device relationship over a network such as the internet. For example, a server may be collective based: portable equipment, broadcast equipment, virtual, application(s) distributed over a broad combination of computing sources, part of a cloud, and/or the like. Similarly, for example, a medical device may be a user based client, portable equipment, broadcast equipment, virtual, application(s) distributed over a broad combination of computing devices, part of a cloud, and/or the like. Additionally, it should be noted that, for example purposes, several of the various embodiments were described as a computer implemented method. However, one skilled in the art will recognize that many various languages and frameworks may be employed to build and use embodiments of the present invention. For example, languages/frameworks may be based upon computing equipment, network equipment, medical devices, combinations thereof, and/or the like.

In this specification, various embodiments are disclosed. Limitations, features, and/or elements from the disclosed example embodiments may be combined to create further embodiments within the scope of the disclosure.

In addition, it should be understood that any figures that highlight any functionality and/or advantages, are presented for example purposes only. The disclosed architecture is sufficiently flexible and configurable, such that it may be utilized in ways other than that shown. For example, the blocks presented in any flowchart may be re-ordered or only optionally used in some embodiments.

Furthermore, many features presented above are described as being optional through the use of "may" or the use of parentheses. For the sake of brevity and legibility, the present disclosure does not explicitly recite each and every permutation that may be obtained by choosing from the set of optional features. However, the present disclosure is to be interpreted as explicitly disclosing all such permutations. For example, a system described as having three optional features may be embodied in seven different ways, namely with just one of the three possible features, with any two of the three possible features or with all three of the three possible features.

Further, the purpose of the Abstract of the Disclosure is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract of the Disclosure is not intended to be limiting as to the scope in any way.

Finally, it is the applicant's intent that only claims that include the express language "means for" or "step for" be interpreted under 35 U.S.C. 112. Claims that do not expressly include the phrase "means for" or "step for" are not to be interpreted under 35 U.S.C. 112.

What is claimed is:

1. A system comprising:
 a) a plurality of medical devices coupled to a computer network, each of the plurality of medical devices comprising:
  i) a device processor; and
  ii) a non-transitory machine readable device medium comprising device instructions configured to cause the device processor to:
   A) generate a device specific Software Bill of Materials (SBOM); and
   B) communicate the device specific SBOM to at least one of a plurality of validator systems;
 b) at least one central authority system coupled to the computer network, each of the at least one central authority system comprising:
  i) a central authority processor; and
  ii) a non-transitory machine readable central authority medium comprising central authority instructions configured to cause the central authority processor to authorize the plurality of validator systems to add a new block to a SBOM blockchain, the SBOM blockchain structured to contain updates to the device specific SBOM; and
 c) the plurality of validator systems coupled to the computer network, the computer network in communication with a vulnerability database, each of the plurality of validator systems comprising:
  i) a validator processor; and
  ii) a non-transitory machine readable validator medium comprising validator instructions configured to cause the validator processor to:
   A) create a local copy of the SBOM blockchain;
   B) build a SBOM hash tree based on data in the SBOM blockchain, the SBOM hash tree comprising:
    a) a root node with an original SBOM; and
    b) at least one leaf node, each of the at least one leaf node comprising a distinct SBOM update;
   C) search the SBOM hash tree for the device specific SBOM;
   D) add the new block to the SBOM blockchain in response to the device specific SBOM not being contained in the SBOM hash tree, the new block comprising a new distinct SBOM update;
   E) validate the new distinct SBOM update based on the vulnerability database in response to the device specific SBOM not being contained in the SBOM hash tree; and
   F) communicate the new block to at least one other validator system in the plurality of validator systems in response to the new block being added to the SBOM blockchain.

2. The system according to claim 1, wherein the device specific SBOM is based on at least one of the following:
 a) a software version;
 b) an installed library;
 c) a library version;
 d) an installed operating system;
 e) an operating system component;
 f) an operating system version;
 g) a patch applied;
 h) a patch version;
 i) installed firmware; and
 j) a firmware version.

3. The system according to claim 1, wherein the device instructions are further configured to cause the device processor to generate the device specific SBOM on a regular basis.

4. The system according to claim 1, wherein the device instructions are further configured to cause the device processor to generate the device specific SBOM according to a schedule.

5. The system according to claim 1, wherein the device instructions are further configured to cause the device processor to generate the device specific SBOM during an idle mode.

6. The system according to claim 1, wherein the device instructions are further configured to cause the device processor to communicate the device specific SBOM upon boot up.

7. The system according to claim 1, wherein the device instructions are further configured to cause the device processor to communicate the device specific SBOM in response to a determination that the device specific SBOM is distinct from a previous device specific SBOM.

8. The system according to claim 1, wherein the device instructions are further configured to cause the device processor to:
 a) generate an assertion; and
 b) communicate the assertion to at least one of the plurality of validator systems.

9. The system according to claim 8, wherein the assertion comprises a digital signature.

10. The system according to claim 1, wherein the validator instructions are further configured to cause the validator processor to:
 a) generate a SBOM score based on: the device specific SBOM, and the vulnerability database; and
 b) add the SBOM score to the new block.

11. The system according to claim 1, further comprising a coordinator system, the coordinator system comprising:
 a) a coordinator processor; and
 b) a non-transitory machine readable coordinator medium comprising coordinator instructions configured to cause the coordinator processor to generate status data.

12. A computer implemented method comprising:
 a) generating a device specific Software Bill of Materials (SBOM) for each of a plurality of medical devices;

b) communicating the device specific SBOM to at least one of a plurality of validator systems;
c) building a SBOM hash tree based on data in a SBOM blockchain, the SBOM hash tree comprising:
   i) a root node with an original SBOM; and
   ii) at least one leaf node, each of the at least one leaf node comprising a distinct SBOM update;
d) searching the SBOM hash tree for the device specific SBOM;
e) adding a new block to the SBOM blockchain in response to the device specific SBOM not being contained in the SBOM hash tree, the new block comprising a new distinct SBOM update;
f) validating the new distinct SBOM update based on a vulnerability database; and
g) communicating the new block to at least one of the plurality of validator systems in response to the new block being added to the SBOM blockchain.

13. The computer implemented method according to claim 12, wherein the device specific SBOM is based on at least one of the following:
a) a software version;
b) an installed library;
c) a library version;
d) an installed operating system;
e) an operating system component;
f) an operating system version;
g) a patch applied;
h) a patch version;
i) installed firmware; and
j) a firmware version.

14. The computer implemented method according to claim 12, further comprising gaining consensus from a majority of the plurality of validator systems, the consensus based on the SBOM blockchain.

15. The computer implemented method according to claim 12, further comprising gaining consensus from a majority of the plurality of validator systems, the consensus based on the vulnerability database.

16. The computer implemented method according to claim 12, further comprising:
a) generating an assertion by one of the plurality of medical devices; and
b) communicating the assertion to at least one of the plurality of validator systems.

17. The computer implemented method according to claim 16, wherein the assertion comprises a digital signature.

18. The computer implemented method according to claim 12, further comprising generating a SBOM score based on: the device specific SBOM, and the vulnerability database.

19. The computer implemented method according to claim 18, further comprising adding the SBOM score to the new block.

20. The computer implemented method according to claim 12, further comprising generating status data.

* * * * *